United States Patent [19]

Hsu

[11] Patent Number: 4,659,662
[45] Date of Patent: Apr. 21, 1987

[54] BATCH FERMENTATION PROCESS

[75] Inventor: Win-Pen Hsu, Woodhaven, N.Y.

[73] Assignee: J. E. Siebel Sons' Company, Inc., Chicago, Ill.

[21] Appl. No.: 593,627

[22] Filed: Mar. 26, 1984

[51] Int. Cl.$^4$ .......... C12P 7/06; C12C 11/00; C12G 1/00; C12N 11/10

[52] U.S. Cl. .................... 435/161; 99/276; 426/15; 426/16; 435/178; 435/182; 435/288

[58] Field of Search ............ 426/15, 16; 435/161, 435/178, 182, 288; 99/276

[56] References Cited

U.S. PATENT DOCUMENTS

| | | | |
|---|---|---|---|
| 490,056 | 1/1893 | Zwietusch | 426/16 |
| 2,228,628 | 1/1941 | Hahn | 435/161 |
| 2,521,397 | 9/1950 | Muller | 426/16 |
| 3,207,605 | 9/1965 | Pollock | 426/16 |
| 3,345,179 | 10/1967 | Pollock | 426/16 |
| 3,437,490 | 4/1969 | Schaus | 426/16 |
| 3,729,321 | 4/1973 | Vacano | 426/16 |
| 3,733,205 | 5/1973 | Shovers | 435/178 X |
| 3,737,323 | 6/1973 | Berdelle-Hilge | 426/16 X |
| 3,959,120 | 5/1976 | Pollock | 99/276 X |
| 4,068,005 | 1/1978 | Chicoye | 426/16 |
| 4,329,918 | 5/1982 | Kuhtreiber | 99/276 |
| 4,350,765 | 9/1982 | Chibata | 435/178 |

OTHER PUBLICATIONS

Hind, H. L., Brewing Science and Practice, vol. II, 4th Inpression, Chapman & Hall, London, 1950, pp. 777–789 & 838–841.
Treran, M. D., Immobilized Enzymes, John Wiley & Sons, N.Y., 1980, pp. 66–71.
S. E. Godtfredsen, et al., "Application of Immobilized Yeast and Yeast Coimmobilized With Amyloglucosidase in the Brewing Process", EBC Congress, pp. 501–511 (1981).

Primary Examiner—David M. Naff
Attorney, Agent, or Firm—Willian Brinks Olds Hofer Gilson & Lione Ltd.

[57] ABSTRACT

Ethanol and fermented beverages such as beer or wine are produced in a batch process by contacting a fermentable substrate with yeast cells encapsulated within a porous, semi-permeable material. Contacting is carrier out in a vessel containing the substrate and a semi-permeable retaining means submerged in the substrate. Encapsulated yeast cells are maintained below the retaining means and in contact with the substrate during fermentation while being freely movable in a portion of the substrate. The retaining means is permeable to the substrate and is substantially impermeable to the encapsulated yeast cells. Preferably, the matrix encapsulating the yeast cells is an alginate gel.

12 Claims, 7 Drawing Figures

BATCH FERMENTATION PROCESS

BACKGROUND OF THE INVENTION

The present invention relates generally to the production of ethanol in a fermentation process. More particularly, the invention relates to the production of fermented beverages such as beers and wines.

As utilized hereinafter, the term "beer" means the potable product of fermentation of brewers wort by appropriate yeasts, and includes specific beverages such as ale, lager, stout and porter. The term "alcoholic malt beverages" also is employed herein as synonymous with beer.

The term "wine" as employed herein means an alcoholic beverage made by yeast fermentation of a must derived from fruits or berries, particularly grapes.

In the description which follows, the production of beer is primarily discussed so as to more easily and readily exemplify and illustrate the essential features of the invention and the differences between the invention and the prior art. As will be appreciated by those of skill in the art, the features discussed also have applicability to wine production, subject to modifications apparent to skilled art workers and/or as pointed out hereinafter, and general applicability to the production of ethanol per se.

Although many nuances exist with respect to particular processing conditions, equipment, yeast strain and the like which differ from one beer producer to the next, the essential feature of all beer production processes is the bringing together of yeast and brewers wort under conditions whereby carbohydrates (sugars) in the wort are converted to alcohol, with evolution of carbon dioxide. For conventional batch processes, this so-called "primary" fermentation step is conducted until a desired degree of attenuation has been achieved, i.e., when fermentation has proceeded to the point where the appropriate degree of sugar conversion to alcohol has occurred and the yeast has consumed a desired quantity of amino acids and other nutrients. Thereafter, the fermented product is matured in processes variously referred to as conditioning, lagering or ruh storage to develop and/or eliminate various aromas and flavors.

The overall time required for beer production is extremely lengthy, sometimes requiring months but more typically requiring from two to three weeks from primary fermentation to final maturation. As a consequence, to achieve the production rates which are demanded by the increasing popularity of beer, large fermentation batches, large and expensive equipment and a number of production lines are required. These features, of course, add significantly to the cost of producing beer.

Another factor which influences the size of fermentation vessels, the overall capacity of beer production processes and the economics of beer production is the problem of foam formation during fermentation. During the course of fermentation, a fine white head appears near the sides of the vessel and above any attemperating coils about 8 to 16 hours after pitching. As fermentation continues, rocky or cauliflower heads of foam appear ("krausen") and eventually reach maximum development ("high krausen"). Depending upon the type, shape and size of the fermentation vessel and the speed of fermentation, the total foam volume can become as much as one-third of the total fermentation volume. At the end of primary fermentation (e.g., 5 to 7 days), the head gradually collapses leaving a dark colored, bitter tasting scum which must be separated from the beer by skimming or suction. While methods are known for minimizing foam formation and facilitating its removal, these too add to the cost and complexity of beer production.

Workers in the art have proposed a number of techniques for achieving more rapid and/or more efficient production of beer, particularly with respect to accelerating the primary fermentation process. For example, it is well known that if the temperature during fermentation (either top or bottom fermentation) is increased, the rate of fermentation can be increased and the fermentation time shortened considerably. It also is known that vigorous exogenous agitation (i.e., agitation above that naturally occurring by virtue of the evolution of carbon dioxide by the fermenting yeast) can accelerate the rate of fermentation. However, equally well known is the fact that beers produced according to these methods have an undesirable "winey" off-flavor which has been related to increased amounts of volatile compounds, such as higher alcohols and esters. In addition, these techniques also promote excessive yeast growth. See, for example, U.S. Pat. No. 4,068,005 of Chicoye, et al., issued Jan. 10, 1978, and U.S. Pat. No. 3,437,490 of Schaus, et al., issued Apr. 8, 1969.

Another approach to reducing the time required to produce beer is to conduct the operation on a continuous basis. According to one proposed form of continuous operation, a number of vessels is employed for the fermentation, each containing a constant volume of wort and yeast in a particular state of fermentation, fresh wort being continuously added at one end of the vessel train and wholly of partly fermented wort being continuously removed from a vessel at the other end of the vessel train. Beers produced according to such methods have not achieved satisfactory flavor, and the process involves complicated equipment and undue risk of contamination as a consequence of the numerous material transfers required and the typically open nature of the vessels.

There also has been proposed a continuous wort fermentation process wherein yeast are immobilized in calcium alginate gels which are then packed in a reactor through which wort is continuously passed. See, S. E. Godtfredsen, et al., "Application Of Immobilized Yeast And Yeast Coimmobilized With Amyloglucosidase In The Brewing Process", EBC Congress, pp. 505–511 (1981). The authors demonstrate, for a small-scale system, a significant increase in output per unit volume fermentation in this process.

As these authors also point out, however, the very speed with which fermentation is conducted in this continuous process can be self-defeating, a problem which also plagues the earlier-described methods for increasing fermentation rates by means of exogenous agitation and/or increased temperature. Thus, while all these methods may result in an increase in the rate at which sugars in the wort are converted to alcohol, they also limit the amount of time during which yeast, in the process of effecting sugar or carbohydrate conversion, performs other beneficial functions. This is particularly so with respect to the action of yeast on compounds such as diacetyl which are produced during fermentation. Diacetyl has a distinct buttery flavor which is unacceptable in beers. In conventional fermentation, within the time period in which yeast convert the wort to a desired degree of attenuation, the yeast absorb diacetyl (and convert diacetyl precursors to diacetyl which is then absorbed). As a result, the fermented wort contains desirably low levels of diacetyl, with further reduction of diacetyl and other compounds such as hydrogen sulfide and acetaldehyde—which are primary components of the "green" aroma of beer after primary fermentation—being accomplished during maturation processes.

Techniques for increasing the speed of fermentation, therefore, limit the time during which the yeast can act upon and absorb diacetyl (and/or precursors of diacetyl) and other compounds. The beer obtained from primary fermentation using these methods has an unacceptably high level of these undesired compounds and must either undergo prolonged maturation to effect reduction of the level of these compounds and/or rely upon other means to effect such reduction. See, e.g., Shovers, et al., U.S. Pat. No. 3,733,205 regarding the addition of diacetyl reductase and its co-factor, nicotinamide adenine dinucleotide, to fermented wort to remove diacetyl. In either case, the net overall processing time and/or expense of beer production is not materially improved over that achieved using conventional fermentation techniques.

Apart from the foregoing, continuous processes involving reactors or columns packed with immobilized yeast also present other difficulties. For example, wort must be very clear before entering the reactor in order to prevent clogging of the reactor and flow lines. In addition, since it is necessary for fresh wort to be continuously available for fermentation, a considerable supply of wort must be on hand at all times, requiring suitable chilled holding vessels to reduce the risk of bacterial contamination and suitable heating devices for warming the wort prior to fermentation. Finally, adoption of a continuous process is rarely economical for breweries operating according to conventional batch techniques, since the required major equipment changes typically will outweigh any benefit of reduced processing time.

There exists a need in the art of beer and wine production for a process which is capable of reducing the overall time required to achieve an acceptable product and which can be adopted by existing producers without need for extensive and costly equipment modifications. In addition, of course, measures effective to reduce the time required to produce acceptable beers and wines also will have applicability in all processes where alcohol production via fermentation is involved.

SUMMARY OF THE INVENTION

It is an object of the present invention to provide a process for producing ethanol and ethanol-containing beverages such as beer or wine.

Another object of the invention is to provide a process for producing ethanol or beer or wine in which the overall time from contacting of a fermentable substrate with yeast to production of the desired fermented product is reduced from that existing in conventional processes.

A specific object of the invention is to provide a process for producing beer or wine in which the overall time from contacting wort or must with yeast to production of a fermented product of acceptable attenuation and flavor is reduced from that existing in conventional beer and wine-making processes.

Another object of the present invention is to provide a process for producing beer and wine which is capable of utilizing a wide variety of yeast strains, many of which cannot be employed in conventional beer and wine-making processes because, notwithstanding desirable attributes thereof, they either sediment too early in the process, do not sediment sufficiently at the end of the fermentation, form a yeast head too early in the fermentation process, and other like problems.

A further specific object of the invention is to provide a process for producing beer or wine in which excessive foam development is prevented.

Yet another specific object is to provide a process for producing beer or wine which is highly economical in terms of rapid fermentation without development of undesired flavors or aromas, production at the end of primary fermentation of a beer or wine which does not require prolonged maturation periods and production of a beer or wine containing low levels of free yeast cells, thereby reducing the burden of subsequent filtration, centrifugation or distillation (for ethanol production).

Yet another object of the invention is to provide a process for producing beer or wine of the type described above, which can be adopted by existing producers without need for costly or extensive equipment modifications.

These and other objects are achieved by a process in which a substrate, capable of being fermented by yeast to produce ethanol or an ethanol-containing potable product, is contacted, in a batch operation, with a plurality of loosely-packed, freely-movable particles comprised of yeast which are immobilized or encapsulated within a semi-permeable matrix material, the contacting being conducted at conditions at which fermentation of the substrate occurs, and wherein the mass of yeast-containing particles is substantially confined within a predetermined region in the fermentable substrate so as to attain intimate contact between yeast-containing particles and fermentable substrate throughout the fermentation process.

According to the invention, as applied to the making of beer for example, the batch fermentation process takes place in vessels conventionally employed in beer-making, such as open or closed vertical or horizontal tanks. Conventional brewers wort (without need for extensive filtration to remove suspended matter) is added to the tank and is pitched with yeast, in the form of a plurality of particles comprised of yeast immobilized in a semi-permeable matrix material. Yeast concentrations are chosen so as to attain a desired degree of attenuation within a generally predetermined period of time, and typically will be the same or, preferably, greater than those employed in conventional beer-making processes during the peak of fermentation. As explained in further detail hereinafter, neither exogenous agitation nor the use of elevated temperatures is required during the process in order to obtain rapid fermentation and, as a consequence, the production of undesired higher alcohols and esters, as well as the production of excessive foam, is minimized.

The overall fermentation and maturation process can be conducted in the same vessel. Desirably low levels of diacetyl and other unwanted compounds are attained in a relatively short time since the overall process reduces yeast growth and reproduction to a minimum. As a result, the production of undesired compounds such as acetaldehyde, hydrogen sulfide and the like, which are yeast-growth dependent and are responsible to a large degree for the "young" or "green beer" aroma, is greatly minimized. This in turn significantly reduces the time, otherwise required in conventional beer processes, of storage needed to reduce or eliminate such compounds. In addition to the foregoing, the present process enables the presence of substantial quantities of yeast (immobilized or encapsulated within the semipermeable matrix material) during maturation; as a result, a rapid and high degree of reabsorption of diacetyl produced during fermentation and/or as a consequence of any yeast growth can be achieved.

As a result of the immobilization of the yeast cells in particles formed from semi-permeable matrix material, removal of yeast from fermented wort is a simple matter of draining the vessel through a screen or filter sized so as to pass fermented wort but retain the yeast-containing particles. The process therefore eliminates the labor-intensive skimming or suction required for yeast removal in top fermentation ale-type processes and, for bottom fermentation processes, eliminates the need to cool the vessel contents to promote yeast settling. In this latter regard, the ability to maintain process temperatures at those at which fermentation and maturation occur at a rapid rate, without need for cooling to remove suspended yeast or to effect centrifugation, is a distinct advantage of the invention which reduces the overall time required to produce beer.

Another feature of the present invention involves the provision of means for maintaining the yeast-containing particles in intimate contact with the wort (and fermented wort) throughout the process. It has been found that, in the initial stages of contact of wort with the yeast-containing particles, the absorption of wort by the yeast causes the particles to settle to the bottom of the fermentation vessel. Thereafter, as the yeast begins to vorogously ferment the sugars in the wort, the rate of alcohol and carbon dioxide production inside the particle exceeds the rate of release of these products to the surrounding fluid. As a result, the particles will float to the surface of the wort. During the progress of active fermentation, the rising particles exert sufficient force to cause particles in upper regions of the wort also to rise and, eventually, a substantial number of such particles lose intimate contact with the wort in the vessel and are not efficiently utilized, if at all, in the fermentation process.

According to the present invention, means are arranged within the batch of wort to prevent ascending yeast-containing particles from rising to the upper level of wort in the vessel. In this way, the particles are always maintained in contact with wort and efficiency of fermentation is enhanced. During fermentation, the upward evolution of alcohol and carbon dioxide and the downward progress of the more dense fermentable sugars in the wort establishes a natural circulation of materials and enhance fermentation rates. In addition, the means employed for achieving this maintained contact can also results in decreased foam formation.

Additional features of the present invention include further means for reducing foam formation through provision of yeast-containing particles at the upper regions of the fermentable substrate.

DETAILED DESCRIPTION OF THE INVENTION

As noted at the outset, the generalized features of the present invention have applicability to all processes in which it is sought to convert all or a portion of a sugar-containing substrate to ethanol by means of a fermentation process and includes processes for making ethanol per se, processes for making beer and processes for making wine. These features are illustrated hereinafter with reference to beer-making processes. In the course of such illustration, a number of particular features are described which have special applicability to beer-making processes.

Figure 1:
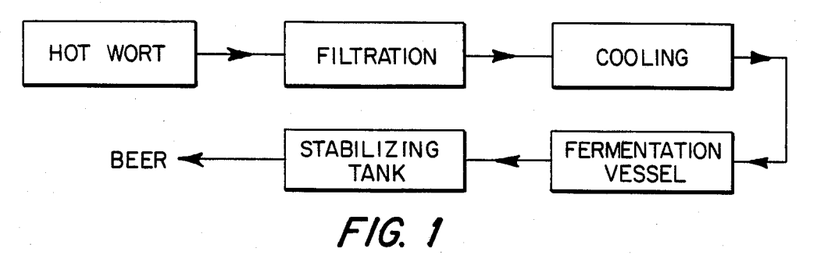
FIG. 1 is a flow diagram of a process for making beer according to the present invention.

In the process of the present invention, as exemplified by the production of beer, a conventional brewers wort is obtained according to known techniques. Thus, for example, a mixture of milled malt and water (and optional adjunct milled cereal grains) is cooked or mashed to obtain a liquified mix in which starch has been enzymatically converted to fermentable sugars such as glucose, maltose and maltotriose. After separation of insoluble solids, the wort is heated (boiled) in a brew kettle (typically with incremental hops or hop extract addition). The hot wort (see FIG. 1) is then filtered using a centrifuge, whirlpool separator, settling tank and filter or other like apparatus. The filtered wort is then cooled to the temperature required for fermentation, the particular temperature being a function of yeast strain, whether top or bottom fermentation is being practiced, and other like factors, and added to an appropriate fermentation vessel for admixture with yeast.

The yeast employed in the process of the present invention is employed in the form of a plurality of particles comprised of yeast cells immobilized or encapsulated within a porous, semi-permeable matrix material.

The particular strain of yeast employed can be selected from any of the known strains for beer or wine production, such as *Saccharomyces cerevisiae* or *Saccharomyces uvarum*, and is not per se critical with respect to the essential features of the present invention. However, a particularly important advantage of the present invention is that it enables the use of a wide variety of yeast strains which generally cannot be satisfactorily employed in conventional beer-making processes. For example, many yeast strains are known which sediment too early in the fermentation process and therefore prolong the time required for complete fermentation. Other yeast strains are known which sediment only to a small degree after fermentation has been effected; this results in large quantities of yeast remaining in suspension in the fermented substrate which must be removed, a costly and time-consuming process. Other yeast strains are known which pass out of suspension into a floating yeast head too early in the fermentation process thereby prematurely arresting fermentation. In accordance with the process of the present invention, however, these inherent limitations of particular yeast strains are readily overcome since the yeast cells are maintained within semi-permeable particles. Thus, for example, inherent sedimentation characteristics of the yeast cells per se which prohibit their use in conventional processes are not problematical in the present invention since the yeast-containing particles as such are used to contribute the requisite characteristics.

The immobilizing or encapsulating matrix for the yeast cells must, in its form of use as an encapsulating matrix, be insoluble in the fermentation substrate (at all stages of fermentation), non-toxic and porous or semi-permeable. The pore size of the matrix material must be sufficiently small to prevent egress of yeast cells encapsulated therein, but sufficiently large to permit fermentable sugars to contact yeast therein and to permit carbon dioxide and alcohol to be liberated therefrom. Generally, the particles—comprised of yeast encapsulated within the matrix material—will be substantially spherical in shape and will have an average diameter of from about 3 to about 5 mm. The average pore size of the particle will generally be less than about $0.5\mu$ to achieve the above-noted retention of yeast cells.

The matrix material also must be sufficiently strong to withstand breakage or breakdown at the conditions of temperature and agitation encountered during use in fermentation. In addition, the matrix must be inert in the sense that it does not react with any materials encountered during fermentation nor liberate any materials to the fermentation medium. Further, the matrix material must be one which is capable of being used to encapsulate or immobilize yeast cells at conditions of encapsulation or immobilization which do not adversely affect the activity of the yeast cells.

A number of materials and processes are known in the art for immobilizing living organisms such as yeast, and are useful in the present invention. See, for example, U.S. Pat. No. 4,350,765 to Chibata, et al. relating to the use of sulfated polysaccharides (such as carageenan, furcellaran and cellulose sulfate), polyacrylamide, sodium alginate, polyvinylalcohol, cellulose succinate and casein succinate as immobilizing or encapsulating materials for yeast. Polymerized acrylates and methacrylates also are useful. See, e.g., U.S. Pat. No. 3,860,490. Gelatin may also be employed as the encapsulating matrix material, as may acryloyl polymers, carboxymethyl cellulose and other like materials. It also is possible to employ light-or radiation-curable resins as the matrix material.

To prepare the encapsulated, yeast-containing particles, yeast cells are mixed with a solution or suspension of the particular matrix material which is then gelled, polymerized or cured, as the case may be, to form droplets of a particular size containing yeast cells encapsulated or immobilized within the matrix material. For example, a liquid mixture of yeast cells and matrix material can be forced through appropriate-sized apertures in a plate to form discrete droplets which are then subjected to conditions at which the matrix material hardens by gelation, cure, polymerization, etc. Alternatively, a vibrating needle can be used to produce discrete droplets of yeast cells/matrix material.

In a preferred embodiment of the invention, sodium alginate is used as the matrix material. A mixture of yeast cells and sodium alginate is drop-wise transferred to a calcium ion-containing solution (e.g., calcium chloride) to effect gelation of the alginate and form discrete particles comprised of yeast cells immobilized or encapsulated within the alginate gel.

The relative proportion of yeast cells to encapsulating matrix for each individual particle is not per se critical subject to possible considerations that, on the one hand, the encapsulation of only a relatively few cells within the matrix might require use of a large quantity of such particles to achieve a particular overall yeast concentration during fermentation and, on the other hand, a too dense packing of cells within the matrix might tend to inhibit the desired ingress and egress of fermentation substrate and products. However, even as to these considerations very few difficulties will be found to exist in practice. Thus, even if few cells are initially encapsulated within each particular particle, it is possible to simply pre-incubate the particles in a suitable yeast growth medium to increase the number of yeast cells therein prior to use of the particles in the fermentation process. On the other hand, even the presence of a high concentration of yeast cells within each particle after the encapsulation process will generally not inhibit the requisite transfer of products to and from yeast cells therein since the nature of the matrix is such as to form an exceedingly open structure which interferes only minimally with the entrapped yeast cells and the passage of small molecular weight compounds into the close vicinity of the cells. Of course, a very high concentration of yeast cells in the particles may result in low overall yeast conversion efficiency relative to the number of yeast cells employed. Typically, the number of yeast cells per particle will be in the range of from about $40 \times 10^6$ to about $600 \times 10^6$, and preferably in the range of from about $100 \times 10^6$ to about $300 \times 10^6$.

In the context of this invention, the terms "encapsulated", "immobilized" and "entrapped" are used interchangeably in describing the relationship of the yeast cells to the semi-permeable matrix material in constituting the yeast-containing particles for use herein. Thus, as to each particular particle the yeast cells are immobilized and entrapped within the matrix material and, to some degree, encapsulated in the sense of being completely within a surrounding layer of the matrix material. As to the yeast-containing particles per se, these are freely-movable within the fermentation substrate. Use herein of any of the above terms is intended to encompass the others.

Figures 2, 3A, 3B:
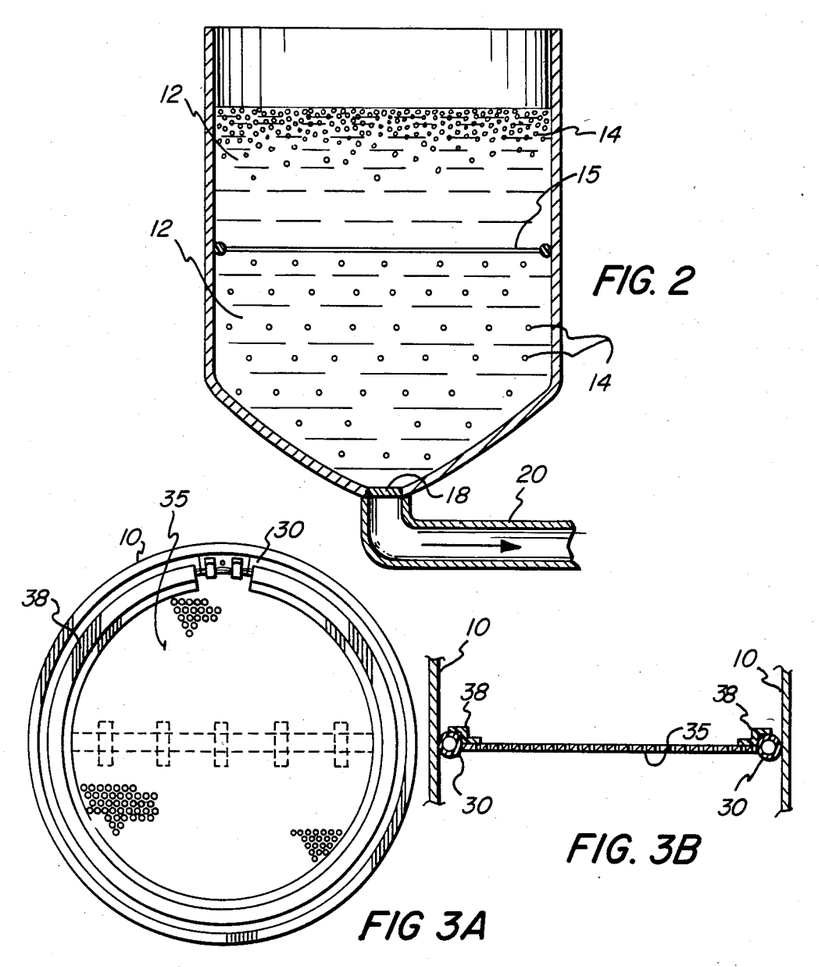
FIG. 2 is a schematic, sectional illustration of a vertical fermentation tank for use in making beer according to the process of the present invention, including means for retaining yeast-containing particles in contact with wort.
FIG. 3A and FIG. 3B are, respectively, plan and sectional views of one particular means for retaining yeast-containing particles in contact with wort in a fermentation vessel.

Continuing with the process of the present invention, fermentation substrate (e.g., wort) and the particles comprised of yeast cells immobilized or encapsulated within a matrix material are contacted in a suitable fermentation vessel, which may be of any type commercially employed in the art of brewing. As shown in FIG. 2, the vessel 10 is a conventional vertical fermentation tank having a tapered bottom which communicates with an exit port protected by a screen or other filter device 18 sized so as to retain the yeast-containing particles 14 in the tank while permitting flow of fermented substrate to a subsequent processing step (e.g., stabilization, packaging) through line 20. Alternatively, of course, the exit port and filter 18 can be arranged at some other suitable location near the bottom of the fermentation vessel.

Fermentation generally will be conducted at temperatures conventionally employed in batch fermentation processes as being optimum conditions for particular strains of yeast, substrate composition, and the like. Temperatures in the range of from about 15° C. to about 20° C. typically will be employed for top fermentations, with temperatures in the range of from about 15° C. to about 16° C. being preferred. For bottom fermentations, temperatures generally will be in the range of from about 7° C. to about 15° C., and preferably from about 10° C. to about 14° C. For wine making, temperatures in the range of from about 7° C. to about 21° C. generally are employed.

A particular advantage of the process of the present invention is that the overall rate of fermentation and maturation is increased without need for resort to elevated temperatures (e.g., in beer-making, temperatures above about 21° C. for top fermentations and 16° C. for bottom fermentations). As a consequence, off-flavors which are known to result from use of such conditions are avoided. Because the yeast cells are employed in the form of discrete particles, the present invention eliminates the need to include as part of the fermentation process conditions which promote aggregation and either settling or rising of the mass of yeast cells to effect their separation from the fermented substrate as the substrate is transferred to other vessels for subsequent processing. Such conditions (e.g., reduced temperature) are generally not those at which optimum fermentation is attained and, as a consequence, it generally requires from about two to three weeks to achieve maturation at the maturation (or conditioning) temperatures employed in conventional processes. The ability to eliminate the need for such conditions being imposed permits an overall decrease in maturation time and, of course, eliminates the need for various equipment and processing (e.g. cooling means) attendant such conditions.

Also as a result of the present invention, a high degree of natural agitation or circulation within the fermentation substrate can be avoided and, hence, the tendency for formation of excessive foam during fermentation is greatly reduced. With decreased foam formation there is also, of course, a desirable decrease in the formation of denatured foam, a dark colored, bitter tasting scum floating on the top of the fermented substrate and also sticking around the sides of the interior walls of the vessel.

As the immobilized yeast cells absorb the fermentable sugars in the substrate and convert them to alcohol and carbon dioxide, there is established in the vessel an upward flow of these less dense products in contradirection to the downward flow of the more dense fermentable sugars. The circulation promoted by this process is enhanced by the fact that the immobilized yeast particles tend to sink to the bottom of the vessel as fermentable sugars are absorbed by the yeast cells therein, and then begin to rise again as the sugars are converted to carbon dioxide and alcohol. These products are produced by the yeast cells at a rate in excess of their rate of liberation from the particles into the fermentation substrate and thus promote levitation of the particles. After their rise through the substrate, the particles evolve sufficient carbon dioxide and alcohol to arrest their rise, begin absorption of additional sugars and traverse downward through the fermentation substrate.

The foregoing assumes that the immobilized yeast cells will, after their initial absorption of sugars and descent and ascent through the fermentation substrate, further absorb fermentable sugars. In accordance with the present invention, it has been found that this condition will not always be met to the degree desired for efficient and rapid fermentation. Thus, rising yeast-containing particles may have the tendency to, in effect, "push" other yeast-containing particles (particularly those at the upper surface of the fermentation substrate which are in the process of absorbing fermentable sugars) out of contact with the fermentation substrate (i.e., to a point above the surface of the substrate and/or above the level at which the fermentable sugars in the substrate exist). As a consequence, these particles do not efficiently, if at all, absorb fermentable sugars, thereby decreasing fermentation rates and decreasing the desired degree of natural agitation or circulation.

In the present invention, therefore, means are provided for maintaining contact between the yeast-containing particles and the fermentable substrate throughout the period of fermentation.

The particular means employed are not critical per se so long as substantially all the yeast-containing particles can be maintained in intimate contact with the substrate during the course of fermentation. Stated in other terms, substantially all the yeast-containing particles should be (broadly) confined to some predetermined area or position within the substrate (the individual particles themselves, however, being freely-movable within such area or position). As such, therefore, the means employed (hereinafter referred to as "retaining means") can comprise any surface or structure substantially impermeable to the yeast-containing particles yet substantially permeable to the fermentable substrate and the products generated via fermentation.

A particularly preferred form of retaining means comprise a semi-permeable surface element in combination with means for maintaining the surface element in a fixed position within the fermentation vessel. The overall retaining means is adapted to engage all inner surfaces of the fermentation vessel such that yeast-containing particles in the vessel cannot by-pass the retaining means.

The surface element of the preferred retaining means is a semi-permeable (generally planar) surface whose apertures are sized sufficiently large so as to permit flow therethrough of fermentable substrate and the products of fermentation, but sufficiently small to substantially resist passage of the yeast-containing particles. The apertures or pores of the surface element may be distributed in any fashion along the surface, and are preferably distributed entirely throughout the surface (i.e., in the nature of a web or screen) so as to maximize the flow of substrate and products therethrough. The surface element may be constructed of any material which will not degrade in the presence of the products and conditions encountered in fermentation and which is inert in the sense of not reacting with products in the fermentation vessel nor liberating any undesired products under conditions of use. The semi-permeable surface may, therefore, be constructed of steel, copper, polymeric materials or the like. In the preferred embodiment of the invention, the semi-permeable surface element is a perforated screen constructed of metallic materials, wherein the perforations are substantially evenly distributed along the surface and are sized such as to resist passage of yeast-containing particles while permitting passage of fermentable substrate and products of fermentation.

As shown in FIG. 2, retaining means 15 is arranged within fermentation vessel 10 after the vessel has been filled with substrate (e.g., wort) 12 and a plurality of yeast-containing particles 14. Retaining means 15 is arranged in the vessel 10 such that it is submerged below the surface of wort in the vessel. Generally, retaining means 15 will be arranged in fixed position within vessel 10 such that from about one-third to about three-fifths the volume of the fermentable substrate will be below the semi-permeable surface of the retaining means. Of course, the substrate and the products of fermentation freely pass through the retaining means.

The retaining means may employ a variety of means for maintaining it in a fixed position within the fermentation vessel. These affixing means can include, for example, one or more reinforced areas along the perimeter of the surface element for engaging rests spaced along the interior wall of the fermentation vessel at a predetermined height. The reinforced areas also can continuously surround the planar surface.

To account for the possibility that for different batch sizes or conditions it may be necessary to utilize the retaining means at a variety of levels within the fermentation vessel, it is preferred that the affixing means be such as to not depend upon the existence of predetermined rests (or other means) integral with the fermentation vessel per se. Preferred affixing means, therefore, will be integral with the surface element itself and be capable of affixing the planar surface to the inner walls of the fermentation vessel at any desired height in the vessel. For this purpose, an inflatable tube member or a series of threaded pressure pads or other like means can be employed in concert with the semi-permeable surface.

In FIGS. 3A and 3B there is shown a preferred embodiment of a retaining means for use in the present invention. The semi-permeable surface 35 consists of a circular perforated screen. An inflatable (e.g., $CO_2$-inflatable) tube 30, which can be constructed of, e.g., rubber or plastic, surrounds the perimeter of screen 35 and is affixed to the screen through use of a continuous tube retainer 38 which is also affixed to tube 30. At full inflation, the tube 30 exerts sufficient pressure against the inner walls of fermentation vessel 10 to hold the screen in a fixed position within the vessel. Tube 30, when deflated, permits movement of the assembly either to a different location in the vessel or for complete removal therefrom. Inflation of tube 30 is achieved through a valve in the tube extending through a hole or a break in tube retainer 38.

Figure 4A:
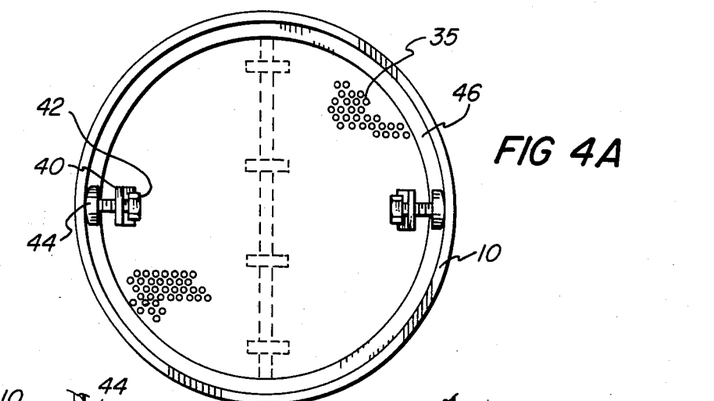
FIG. 4A and FIG. 4B are, respectively, plan and sectional views of another means for retaining yeast-containing particles in contact with wort in a fermentation vessel.
Figure 4B:
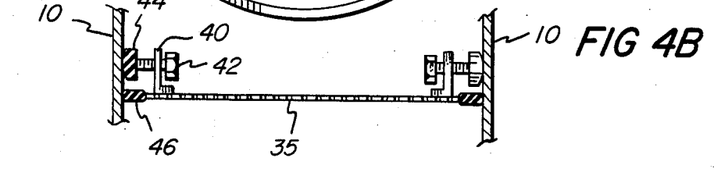

FIGS. 4A and 4B show an alternate retaining means arrangement in which screen 35 has, at two or more points at its periphery, attached threaded lugs 40 containing a threaded bolt 42. At the end of the bolt a cap 44 is tapped or threaded (preferably made of rubber or plastic) which engages the inner wall of the fermentation vessel 10 when bolt 42 is threaded through lug 40. As shown in FIG. 4B, it is preferred that screen 35 be surrounded along its perimeter with a soft gasket material 46. By unthreading of one or more of the bolts, the retaining means can be moved to different locations within the fermentation vessel or be entirely removed from the fermentation vessel.

In operation, yeast-containing particles can first be introduced into the vessel, followed by insertion of the retaining means and introduction of substrate. The retaining means also can be inserted prior to charging of the vessel with yeast-containing particles, provided that an entry port therefor is present below the level of the retaining means. Still further, the retaining means itself can be arranged to have an opening port (closed during operation) through which yeast-containing particles can be charged to the substrate, below the level of the retaining means.

As shown in FIG. 4A, the screen or other semi-permeable planar surface can be hinged so as to be foldable, at least to some degree, to facilitate placement in and removal from the fermentation vessel.

Figure 5:
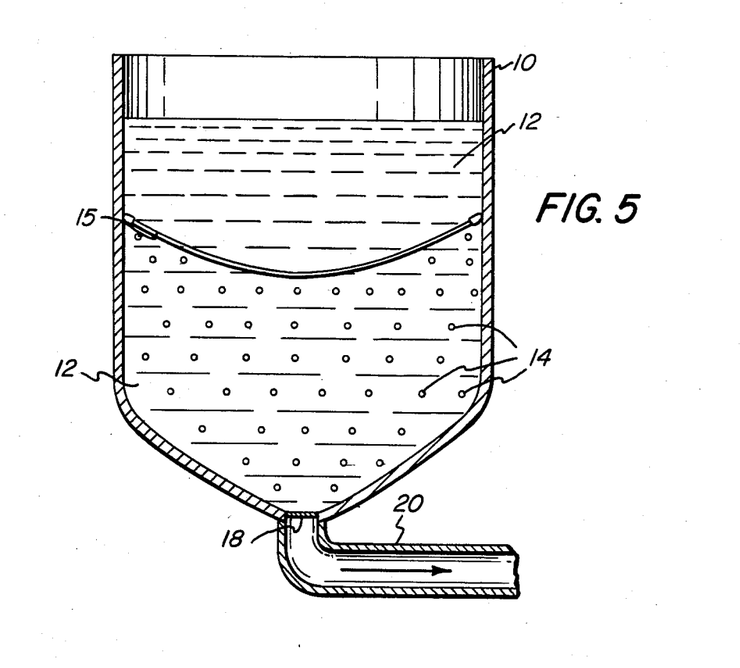
FIG. 5 is a schematic, sectional illustration of a vertical fermentation tank for use in making beer according to the present invention, showing alternative means for retaining yeast-containing particles in contact with wort during fermentation.

With reference to FIG. 5, it will be seen that the retaining means also can comprise semi-permeable surfaces other than rigid screens or the like and, for example, can comprise flexible semi-permeable materials arranged at predetermined levels or areas within the fermentable substrate.

In the process of the present invention, the semi-permeable nature of the retaining means generally is such as to also assist in the break-up of foam which may be generated during fermentation and hence reduce the presence of denatured foam at the upper surfaces of the fermentation substrate. In accordance with a further aspect of the present invention, foam reduction can be aided by providing yeast-containing particles at the upper surfaces of the substrate during fermentation and maturation. Preferably, the yeast-containing particles (of the same type utilized in the fermentation process or of some different type) will be added in an amount sufficient to form a layer covering the entire surface of the fermentable substrate and extending to a depth of from about 2 to 12 inches within the substrate (see FIG. 2).

In the process of the present invention, the fermentation substrate is pitched with an appropriate concentration of yeast cells (i.e., with an appropriate number of particles in which yeast cells are encapsulated or immobilized) to obtain a desired degree of attenuation in the shortest possible time. Generally, the concentration of yeast-containing particles in the wort or other fermentation substrate will be in the range of from about 10% to about 50% (w/v), and preferable in the range of from about 20% to about 30% (w/v).

The entire fermentation and maturation process preferably will be conducted in a single vessel and will continue until a suitably chosen end-point is reached, i.e., reduction in diacetyl content below about 0.15 ppm. When the desired degree of attenuation and diacetyl concentration is reached, the contents of the vessel are drained through a suitable port in the bottom portion of the vessel, over which is arranged a suitable screen or filter sized so as to retain yeast-containing particles yet pass the liquid contents of the vessel. Alternatively, this screen or filter can be arranged outside the fermentation vessel at some point along the path to the next subsequent processing step (e.g., in line 20 of FIG. 2). In another alternative, the screen or filter is arranged in the fermentation vessel at a point above the exit port, in a manner such that all materials in the fermentation vessel in which yeast-containing particles are dispersed or suspended must pass through the screen or filter.

During the process of the invention, if conducted in a single fermentation vessel, temperatures can, if desired, be varied throughout the process to attain optimum fermentation and, thereafter, optimum maturation.

The fermented substrate, separated from yeast-containing particles, is then treated according to conventional techniques of filtration, chillproofing, anti-oxidation, foam enhancement and other like processes, prior to bottling or canning.

The yeast-containing particles remaining in the vessel are then washed with cold water, buffered water or saline through a conventional jet spray before the next batch of new fermentation substrate is added to the vessel. In this manner, the yeast-containing particles can be continuously used until their fermentation and maturation efficiencies have decreased to a point where the fermentation/maturation can no longer be conducted within desirably short predetermined time limits.

In an alternative method of practicing the invention, a separate vessel can be used for maturation, in which case the fermented beer can be transferred from the fermentation vessel to a (maturation) vessel containing yeast-containing particles at a lower concentration than employed in the primary fermentation vessel. Preferably, the maturation vessel also will include retaining means as earlier described with reference to the fermentation vessel.

The process of the present invention is further described with respect to the following illustrative examples relating to beer and wine production.

EXAMPLE 1

In a control beer fermentation, 10 liters of a commercial high gravity wort (15.5° Plato) was aerated and pitched with a strain of Saccharomyces carlsbergensis at about 10 million yeast cells per ml. The wort was then fermented at 15° C. (59° F.) for 9–10 days until the diacetyl content was reduced to less than 0.15 ppm. The fermented wort was then kept in a 2°–4° C. refrigerator for two weeks for maturation and for allowing the yeast cells to precipitate.

In the fermentation process of the present invention, immobilized yeast particles were prepared as follows: one hundred ml of a freshly grown yeast sediment and 200 ml of 1.25 percent (w/v) sodium alginate solution were blended in a Waring blender and extruded as drops into 80 mM $CaCl_2$ solution. The droplets were hardened to become yeast particles as soon as the drops were mingled with the solution under circulation.

About 2.6 Kg of the above yeast particles were placed inside a fermentation vessel and a particles retaining screen was then attached above the yeast particles. Additionally about 500 grams of the same yeast particles were placed on the upper side of the retaining screen. Ten liters of the aforementioned commercial wort, without pre-aeration, were introduced into the above-mentioned fermentation vessel. The wort was fermented and matured at 15° C. (59° F.) for 7 days.

Generally, in the process of the present invention, the wort was completely fermented within 48 hours and an additional five days were allowed for beer maturation. The diacetyl contents were 0.55 ppm after 6 hours, 1.11 ppm after 16 hours, 1.33 ppm after 24 hours and 0.12 ppm after 7 days.

The two beers obtained by the conventional method and the process of the invention were then finally filtered and diluted with carbonated water to about 11.5° Plato, original gravity equivalent. The beers were chillproofed, carbonated and bottled by the conventional method.

The beer obtained by the process of the present invention was smoother than the conventionally fermented beer and was found to be matured without any green beer characteristics. The analyses of the two beers (Table I) show very little difference in physical and chemical compositions.

TABLE I

|  | Control | Inventive Process |
|---|---|---|
| Original Extract, Calc., % | 11.5 | 11.4 |
| Apparent Extract, % | 2.08 | 2.27 |
| Real Extract, % | 3.90 | 4.04 |
| Apparent Degree of Fermentation, % | 81.9 | 80.1 |
| Real Degree of Fermentation, % | 66.1 | 64.6 |
| Alcohol by Volume, % | 5.00 | 4.84 |
| Alcohol by Weight, % | 3.92 | 3.79 |
| Color °SRM | 3.9 | 3.9 |
| Reducing Sugars, % | 0.97 | 0.92 |
| Protein, % | 0.37 | 0.31 |
| Acid as Lactic, % | 0.21 | 0.16 |
| pH Value | 4.26 | 4.04 |
| Bitterness Units, B.U. | 11.9 | 10.0 |
| Diacetyl, ppm | 0.11 | 0.08 |

EXAMPLE 2

The following five experiments were conducted to demonstrate the difference in fermentation speed with and without the yeast particles retaining means in the beer production.

In each experiment, two vessels were used, one vessel containing no retaining means and the other vessel containing a retaining means. In each vessel, 700 ml of a commercial high gravity wort were fermented with 300 grams of the immobilized yeast particles prepared in the same manner as described in Example 1.

As shown in Table II, the worts in the vessels with a retaining means were fermented to the desired attenuation while the worts in the vessels containing no retaining means were not fully (completely) fermented in 48 hours.

TABLE II

| | | Specific gravity (°Plato) of the fermentation wort | |
|---|---|---|---|
| Experiment | Hours | No Retaining Means | With Retaining Means |
| 1 | 0 | 15.5 | 15.5 |
|  | 24 | 9.0 | 4.4 |
|  | 48 | 4.5 | 3.4 |
| 2 | 0 | 15.5 | 15.5 |
|  | 24 | 7.0 | 4.3 |
|  | 48 | 4.0 | 3.3 |
| 3 | 0 | 15.0 | 15.0 |
|  | 24 | 8.1 | 5.2 |
|  | 48 | 4.6 | 2.6 |
| 4 | 0 | 14.9 | 14.9 |
|  | 24 | 9.0 | 4.5 |
|  | 48 | 4.0 | 3.0 |
| 5 | 0 | 15.2 | 15.2 |
|  | 24 | 9.7 | 4.7 |
|  | 48 | 4.3 | 3.2 |

EXAMPLE 3

In wine fermentation, a concentrated grape juice recommended for the production of Riesling type wine was used. Following the suggested formulation, 182 ml of the juice concentrate and 74 grams of sucrose were dissolved in each liter of warm water. The prepared must was cooled to 15° C. (59° F.) and pitched with a wine yeast prepared from an active dry yeast of Saccharomyces cerevisiae. The yeast concentration at the time of pitching was about $40 \times 10^6$ yeast cells per ml of the must.

The above wine yeast was also used to prepare immobilized yeast particles following the procedure described in Example 1. In the fermentation process of the present invention, one liter of the above must was transferred to a fermentation vessel which contained 300 grams of the yeast particles under a retaining screen and 100 grams of the yeast particles above the retaining screen. As shown in Table III the difference in fermentation speed between the conventional and the process according to the invention were very significant.

TABLE III

| | Specific gravity (°Brix) of the fermentation must | |
|---|---|---|
| Day | Conventional | Invention Process |
| 0 | 19.0 | 19.0 |
| 1 | 16.1 | 6.3 |
| 2 | 13.3 | 0.3 |
| 3 | 11.1 | −1.7 |
| 7 | 4.1 | −2.0 |
| 8 | 2.9 | −2.0 |
| 10 | 2.2 | — |
| 13 | −0.7 | — |
| 17 | −1.3 | — |
| 20 | −1.5 | — |

What is claimed is:

1. A process for producing an ethanol-containing product by batch fermentation, comprising the steps of:
   (a) providing a fermentable substrate containing compounds which can be converted to ethanol in the presence of yeast;
   (b) providing a plurality of yeast-containing particles comprised of living yeast cells substantially encapsulated within a porous, semi-permeable matrix material which is insoluble in said fermentable substrate, the pores of said matrix material being sized so as to retain therein said yeast cells yet be permeable to said compounds in the fermentable substrate;
   (c) contacting a batch of said fermentable substrate with a plurality of said yeast-containing particles at conditions at which said yeast cells effect conversion of compounds in said substrate to ethanol and carbon dioxide, said contacting being performed in a vessel in which is arranged a retaining means, said retaining means comprising a semi-permeable surface which is permeable to said substrate and substantially impermeable to said yeast-containing particles, said retaining means being submerged within said substrate and effective for substantially maintaining said yeast-containing particles in contact with said fermentable substrate below said retaining means for the duration of the fermentation process, said yeast-containing particles being freely-movable within at least a portion of said substrate during said fermentation process and said yeast-containing particles floating upward in the substrate toward the retaining means as carbon dioxide is formed within the particles; and
   (d) continuing said contacting of said fermentable substrate and yeast-containing particles until a desired degree of conversion of said substrate to an ethanol-containing product is achieved.

2. A process for producing a fermented beverage product by batch fermentation, comprising the steps of:
   (a) providing a fermentable substrate selected from the group consisting of brewers wort and must;
   (b) providing a plurality of yeast-containing particles comprised of living yeast cells substantially encapsulated within a porous, semi-permeable matrix material which is insoluble in said fermentable substrate, the pores of said matrix material being sized so as to retain therein said yeast cells yet be permeable to sugars in the fermentable substrate;
   (c) contacting a batch of said fermentable substrate with a plurality of said yeast-containing particles at conditions at which said yeast cells effect conversion of sugars in said substrate to carbon dioxide and ethanol, said contacting being performed in a vessel in which is arranged a retaining means, said retaining means comprising a semi-permeable surface which is permeable to said substrate and substantially impermeable to said yeast-containing particles, said retaining means being submerged within said substrate and effective for substantially maintaining said yeast-containing particles in contact with said fermentable substrate below said retaining means for the duration of the fermentation process, said yeast-containing particles being freely-movable within at least a portion of said substrate during said fermentation process and said yeast-containing particles floating upward in the substrate toward the retaining means as carbon dioxide is formed within the particles; and
   (d) continuing said contacting of said fermentable substrate and yeast-containing particles until a desired degree of attenuation and maturation is achieved.

3. The process according to claim 2 wherein said fermentable substrate comprises brewers wort.

4. The process according to claim 2 wherein said fermentable substrate comprises must.

5. The process according to claim 3 wherein the contacting of said fermentable substrate and said yeast-containing particles is effected in the absence of exogenous agitation.

6. The process according to claim 3 wherein the contacting of said fermentable substrate and said yeast-containing cells is conducted at a substrate temperature in the range of from about 15° C. to 20° C. for a top fermentation process and in the range of from about 7° C. to about 15° C. for a bottom fermentation process.

7. The process according to claim 2 wherein said fermentable substrate comprises between wort and wherein said contacting is conducted for a time sufficient to reduce the level of diacetyl in the fermented beverage to less than about 0.15 parts per million.

8. The process according to claim 2 further comprising the step of passing the fermented beverage resulting from step (d) through a filter means effective to separate said yeast-containing particles from said fermented beverage.

9. The process according to claim 2 wherein said matrix material comprises alginate gel.

10. The process according to claim 2 further comprising the step of providing a quantity of yeast-containing particles at the upper surface of said fermentable substrate effective to reduce the formation of foam or the presence of excessive denatured foam at the upper surface of said substrate.

11. A process for producing beer by batch fermentation, comprising the steps of:
   (a) providing a brewers wort comprised of fermentable sugars;
   (b) providing a plurality of yeast-containing particles comprised of living yeast cells substantially encapsulated within a porous alginate gel, the pores of which are sufficiently small so as to retain yeast cells therein and sufficiently large to permit the yeast cells therein to absorb said fermentable sugars from said brewers wort, the size and density of said yeast-containing particles being such that, in contact with said brewers wort, said particles are capable of natural movement and suspension;

(c) contacting a batch of said wort with a plurality of said yeast-containing particles in a vessel at conditions at which said yeast cells effect conversion of fermentable sugars to products comprising carbon dioxide and alcohol, said contacting being conducted in the presence of retaining means arranged within said vessel, contiguous with the inner surfaces thereof, and submerged below the surface of said wort to confine said yeast-containing particles to an area of the vessel below said retaining means, said yeast-containing particles floating upward in the substrate toward the retaining means as carbon dioxide is formed within the particles and said yeast-containing particles being freely-movable within at least a portion of said substrate during said fermentation process, said retaining means comprising a semi-permeable surface in association with means for affixing said surface at a predetermined level within the vessel, said semi-permeable surface being sized so as to be impermeable to said yeast-containing particles but permeable to said brewers wort and the products produced by the action of yeast on said wort; and (d) continuing said contacting until a desired degree of conversion of fermentable sugars in said wort to alcohol is attained and the level of diacetyl in the fermented product is reduced to less than 0.15 ppm.

12. The process for producing beer according to claim 11 further comprising the step of providing at the upper surfaces of said wort during the fermentation process a quantity of yeast-containing particles effective to reduce foam formation and the presence of excessive denatured foam at the upper surface of said wort.

* * * * *

UNITED STATES PATENT AND TRADEMARK OFFICE
CERTIFICATE OF CORRECTION

PATENT NO. : 4,659,662
DATED : April 21, 1987
INVENTOR(S) : Wen-Pin Hsu

It is certified that error appears in the above-identified patent and that said Letters Patent is hereby corrected as shown below:

On the cover sheet, please delete "Win-Pen Hsu" and substitute therefor --Wen-Pin Hsu--.

IN THE ABSTRACT

On line 4, please delete "carrier" and substitute therefor --carried--.

IN THE BACKGROUND OF THE INVENTION

In column 2, line 35, please delete "of" and substitute therefor --or--.

IN THE SUMMARY OF THE INVENTION

In column 5, line 37, please delete "vorogously" and substitute therefor --vigorously--.

In column 5, line 60, please delete "results" and substitute therefor --result--.

UNITED STATES PATENT AND TRADEMARK OFFICE
CERTIFICATE OF CORRECTION

PATENT NO. : 4,659,662

DATED : April 21, 1987

INVENTOR(S) : Wen-Pin Hsu

It is certified that error appears in the above-identified patent and that said Letters Patent is hereby corrected as shown below:

IN THE CLAIMS

In column 16, line 44, please delete "between" and substitute therefor --brewers--.

Signed and Sealed this

Twenty-first Day of November, 1989

Attest:

JEFFREY M. SAMUELS

Attesting Officer      Acting Commissioner of Patents and Trademarks